United States Patent
Sandholm et al.

(10) Patent No.: US 6,899,254 B1
(45) Date of Patent: May 31, 2005

(54) VENTING SEAL FOR DISPENSER

(75) Inventors: Albert E. Sandholm, Brooklyn, CT (US); Charles M. Frey, Bozrah, CT (US)

(73) Assignee: Plas-Pak Industries, Inc., Norwich, CT (US)

( * ) Notice: Subject to any disclaimer, the term of this patent is extended or adjusted under 35 U.S.C. 154(b) by 0 days.

(21) Appl. No.: 10/761,693

(22) Filed: Jan. 20, 2004

(51) Int. Cl.[7] .............................................. G01F 11/00
(52) U.S. Cl. ...................... 222/387; 222/386; 222/326
(58) Field of Search ................................ 222/386, 387, 222/386.5, 326–327, 340, 256, 253, 481.5; 604/218, 229, 228, 238, 221–222, 225–226, 604/190

(56) References Cited

U.S. PATENT DOCUMENTS

| | | | |
|---|---|---|---|
| 3,075,675 A * | 1/1963 | Wormser et al. | 222/327 |
| 3,949,897 A | 4/1976 | Shaw et al. | |
| 4,402,431 A * | 9/1983 | Wiegner et al. | 222/207 |
| 4,632,672 A * | 12/1986 | Kvitrud | 604/222 |
| 4,657,161 A * | 4/1987 | Endo et al. | 222/256 |
| 4,685,594 A * | 8/1987 | Czech | 222/182 |
| 4,747,511 A | 5/1988 | Dutt et al. | |
| 4,792,065 A * | 12/1988 | Soehnlein et al. | 222/387 |
| 4,819,836 A | 4/1989 | Meckenstock | |
| 5,000,355 A | 3/1991 | Pritchard | |
| 5,042,695 A * | 8/1991 | Battegazzore | 222/259 |
| 5,150,823 A | 9/1992 | Sugita | |
| 5,170,913 A * | 12/1992 | Spatz | 222/209 |
| 5,178,305 A | 1/1993 | Keller | |
| 5,209,376 A | 5/1993 | Dirksing | |
| 5,238,003 A * | 8/1993 | Baidwan et al. | 600/578 |
| 5,377,880 A * | 1/1995 | Moretti | 222/207 |
| 5,569,236 A | 10/1996 | Kriesel | |
| 5,899,349 A | 5/1999 | Moore | |
| 5,983,059 A | 11/1999 | Oka et al. | |
| 6,145,688 A | 11/2000 | Smith | |
| 6,546,892 B2 | 4/2003 | Kelly et al. | |
| 6,598,766 B1 * | 7/2003 | Brugner | 222/326 |

* cited by examiner

Primary Examiner—Frederick Nicolas

(57) ABSTRACT

A dispenser includes a container providing a cavity and a discharge opening at one end. A piston in the cavity has a peripheral wall portion sealing against the inner wall of the container and a centrally disposed passage therethrough. A sealing plug of resiliently deformable material is seated in the passage and has a peripheral flange about the front end adjacent the discharge opening. The flange bears upon the surface of the front wall of the piston about the passage to effect a seal therebetween. A filler push rod bears upon the surface of the sealing plug is movable to move the flange of the plug away from the surface of the piston to allow air to vent through the passage about the periphery of the plug.

11 Claims, 6 Drawing Sheets

VENTING SEAL FOR DISPENSER

BACKGROUND OF THE INVENTION

The present invention relates to dispensing devices such as syringes and the like, and, more particularly to such a dispenser in which there is provided means for evacuating air from the cavity after product has been placed therein and the piston inserted thereabove.

As is well known, syringes and like dispensers in which a plunger or push rod is pushed to dispense the contents are widely used for many applications from medicine to industrial activities. Generally, such dispensers will have a barrel or other container providing the cavity, a dispensing opening at one end, and the other end is open end for insertion of the product thereinto. Because it is desirable to avoid leakage around the piston as it is moved forward to dispense the material, air is trapped below the piston as it is pushed into the cavity above the material.

In order to eliminate the air from the cavity, various procedures have been utilized including a vent in the piston which is subsequently closed. If the vent is not completely closed, there are obvious problems when the syringe is put into use. If the air is not completely evacuated, it may interfere with the operation of the dispenser by causing disruptions in a smooth flow.

Accordingly, it is an object of the present invention to provide a novel and improved dispensing assembly in which air may be readily removed from the cavity after the cavity has been filled with the desired product and the piston placed therein.

It is also an object to provide such a dispenser which can be fabricated readily and economically.

Another object is to provide such a dispenser in which the sealing elements and the venting element can be overmolded on the basic piston.

SUMMARY OF THE INVENTION

It has now been found that the foregoing and related objects may be readily attained in a dispenser comprising a container providing a cavity and a discharge opening at one end. A piston in the cavity has a peripheral wall portion sealing against the inner wall of the container defining the cavity, and the piston has a front wall with a centrally disposed passage therethrough. A sealing plug of resiliently deformable material seated in the piston passage, and it has a peripheral flange out the front end thereof adjacent the discharge opening. This flange bears upon the surface of the front wall of the piston about the passage to effect a seal therebetween. A filler push rod extends into the container cavity and has one end bearing upon the rear surface of the sealing plug, and the push rod is movable against the other or inner end of the plug to move the flange of the plug away from the surface of the piston to allow air to vent through the passage about the periphery of the plug.

Preferably, the front wall of the piston is concave, and the piston has an annular body portion connected to the peripheral wall by the front wall. The front wall has a center portion radially inwardly of the annular body portion and in which the passage is provided.

Generally, the piston peripheral wall portion has at least one sealing ring extending thereabout at its end adjacent the front wall. Preferably, the piston peripheral wall portion has a second sealing ring extending thereabout adjacent the other end thereof, and the sealing rings are formed from a resiliently deflectable resin.

Desirably, the plug is seated in a recess in the central portion of the front wall of the piston. The plug has a convex face on its front end and a multiplicity of axial projections on the other end against which the filler push rod bears after filling of the cavity and causes the deflection of the flange to release any entrapped air in the cavity.

The filler push rod has a pusher body with a front end having a central projection thereon dimensioned to bear only upon the plug. The dispenser push rod used for the dispensing of the contents bears upon the body of the piston and does not effect deflection of the flange of the plug. Preferably, the body of the plug has a peripheral surface tapering to a reduced diameter at its rear end to facilitate air flow.

DETAILED DESCRIPTION OF THE ILLUSTRATED EMBODIMENT

Figure 1:
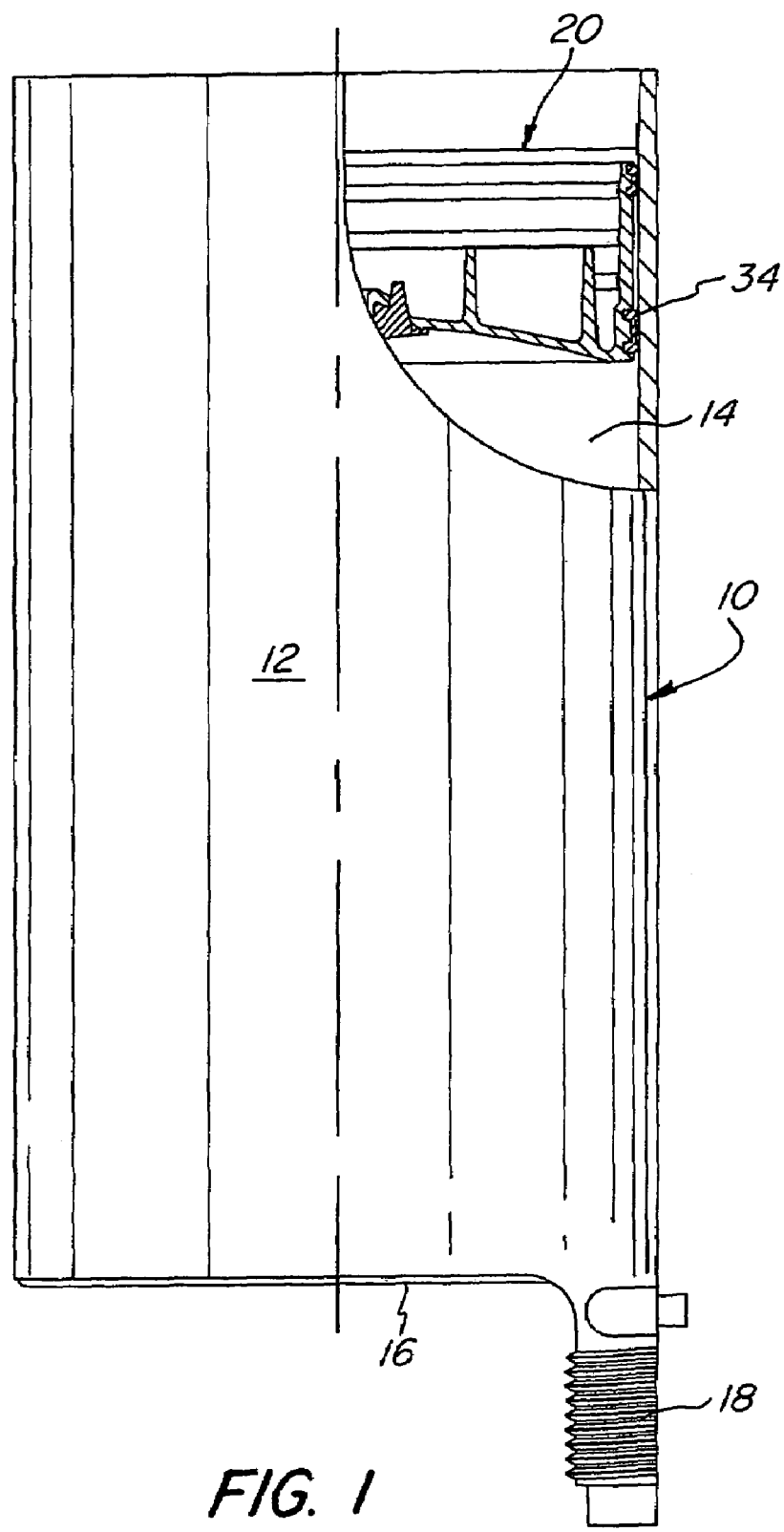
FIG. 1 is a side elevational view of one barrel of a dual barrel syringe-type dispenser omitting the push rod with a portion of the container wall broken away to show the novel piston assembly of the present invention.
Figure 3:
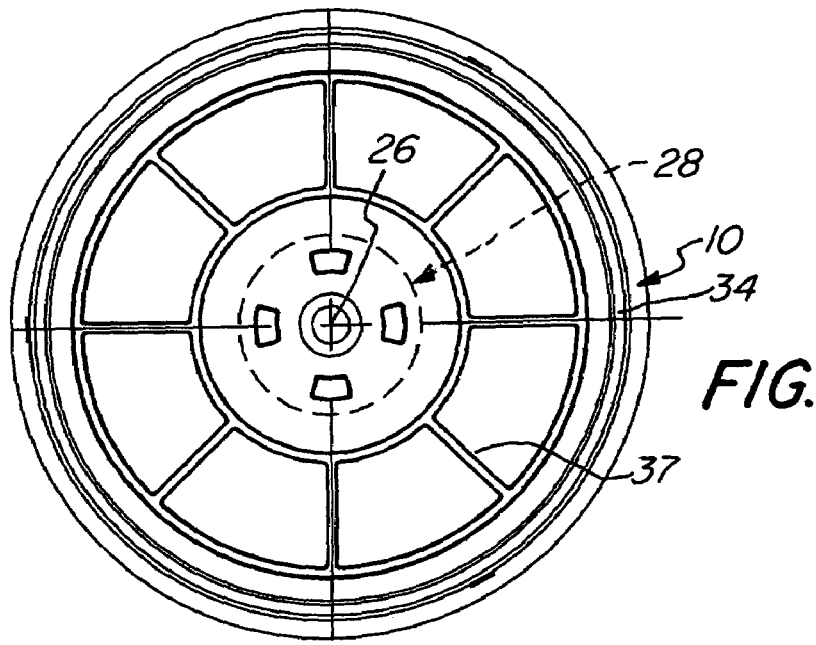
FIG. 3 is a top plan view of the piston assembly of FIG. 1.
Figure 2:
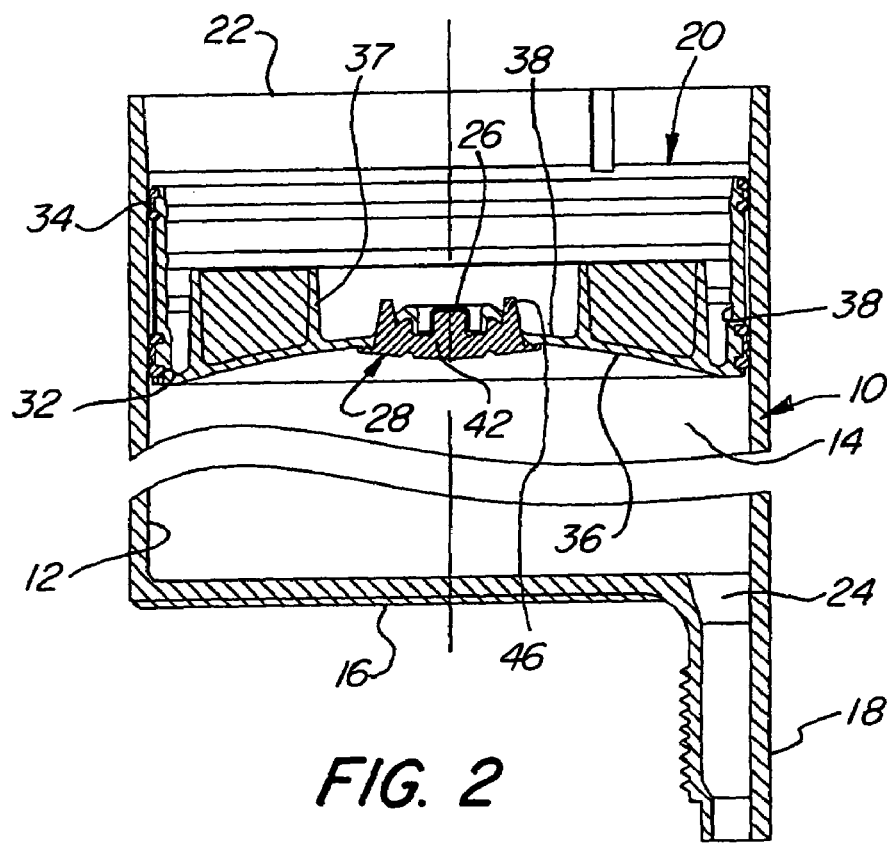
FIG. 2 is a fragmentary axial cross sectional view of the dispenser of FIG. 1.
Figure 5:
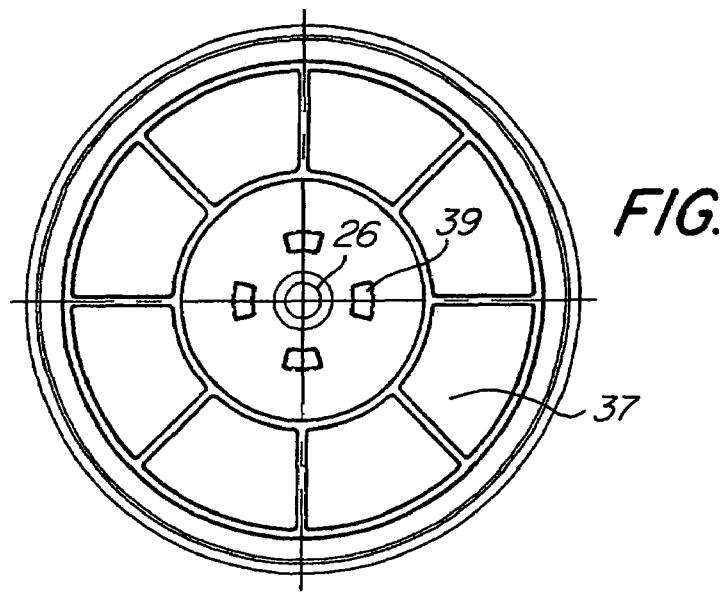
FIG. 5 is a top plan view of the piston prior to the overmolding step.
Figure 4:
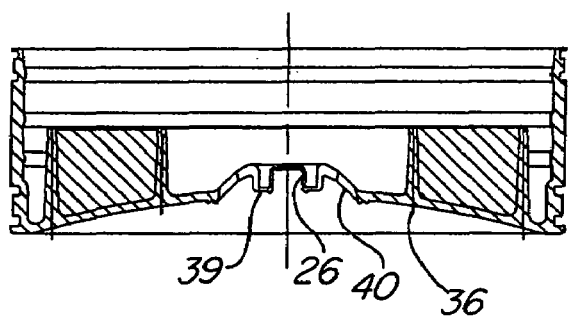
FIG. 4 is a cross sectional view of the piston prior to overmolding the sealing rings and plug.
Figure 6:
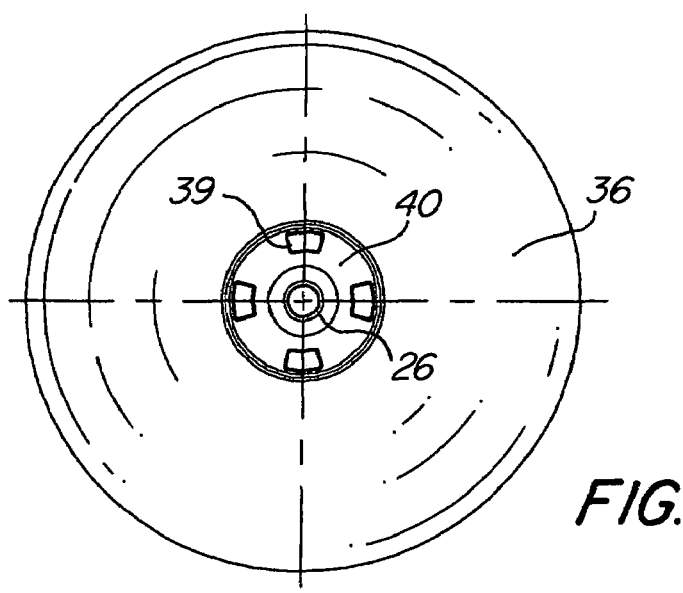
FIG. 6 is a plan view of the piston prior to the overmolding step.
Figure 7:
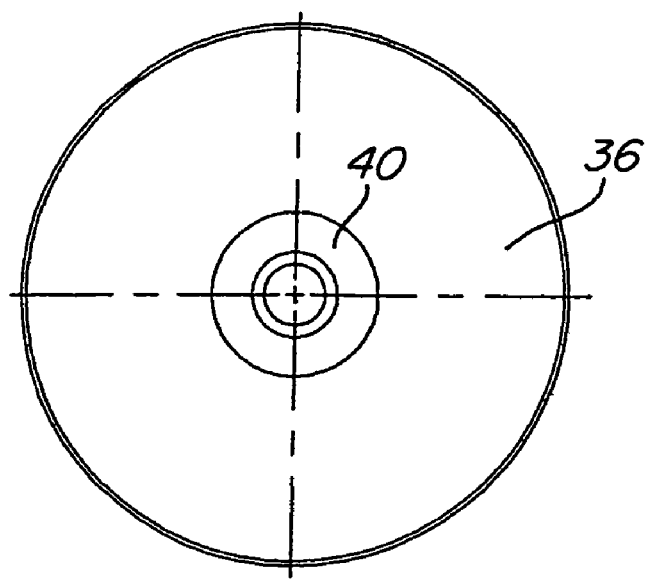
FIG. 7 is a bottom plan view of the piston with the plug seated therein.

Turning first to FIGS. 1 and 2 of the attached drawings, therein illustrated is one barrel of a two barrel dispensing syringe comprising a generally cylindrical container generally designated by the numeral 10 having a peripheral wall 12 defining a cavity 14 therein, an end wall 16 with one-half of dispenser neck 18. Slidably seated within the cavity 14 is a piston generally designated by the numeral 20. Not shown is a conventional push rod which extends through the open end 22 of the container 10 to bear upon and push the piston 20 towards the end wall 16 and thereby dispense the material stored in the cavity 14 through a discharge opening 24 into the neck 18 upon which is threadably mounted a mixer/nozzle (not shown).

As seen in FIG. 2, the piston 20 is of circular cross section with a central orifice 26 in which is seated a plug generally designated by the numeral 28. The peripheral wall 30 of the piston 20 has two pairs of axially spaced grooves 32 formed therein and sealing rings 34 are seated therein. The piston 20 has a front wall 36 connecting the peripheral wall 38 to the annular body portion 37 with radially extending spokes and providing a central portion 38 in which is formed the orifice 26 and four circumferentially spaced openings 39. The front wall 36 is of generally concave configuration and has a recessed portion 40 about the orifice 26 in which the body portion 42 of the plug 28 seats.

The front end of the plug 28 adjacent the end wall 16 has a convex curvature providing a peripheral flange 44 which seats against the front wall 36 of the piston 20 and four prongs 46 on the rear end of the plug 28 extend through the front wall 36.

Figure 8:
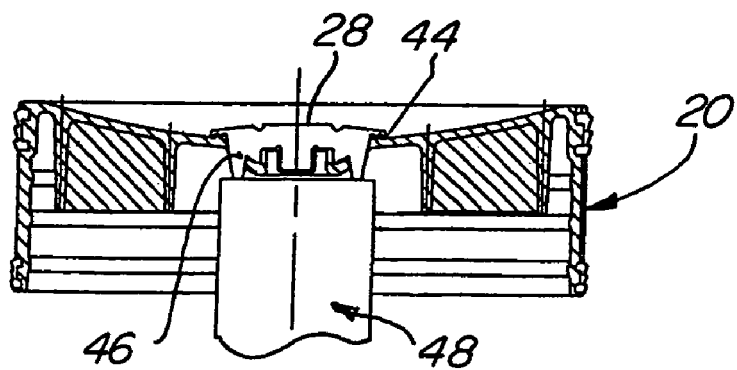
FIG. 8 is a sectional view of a fragmentarily illustrated filler push rod seated against the plug.
Figure 9:
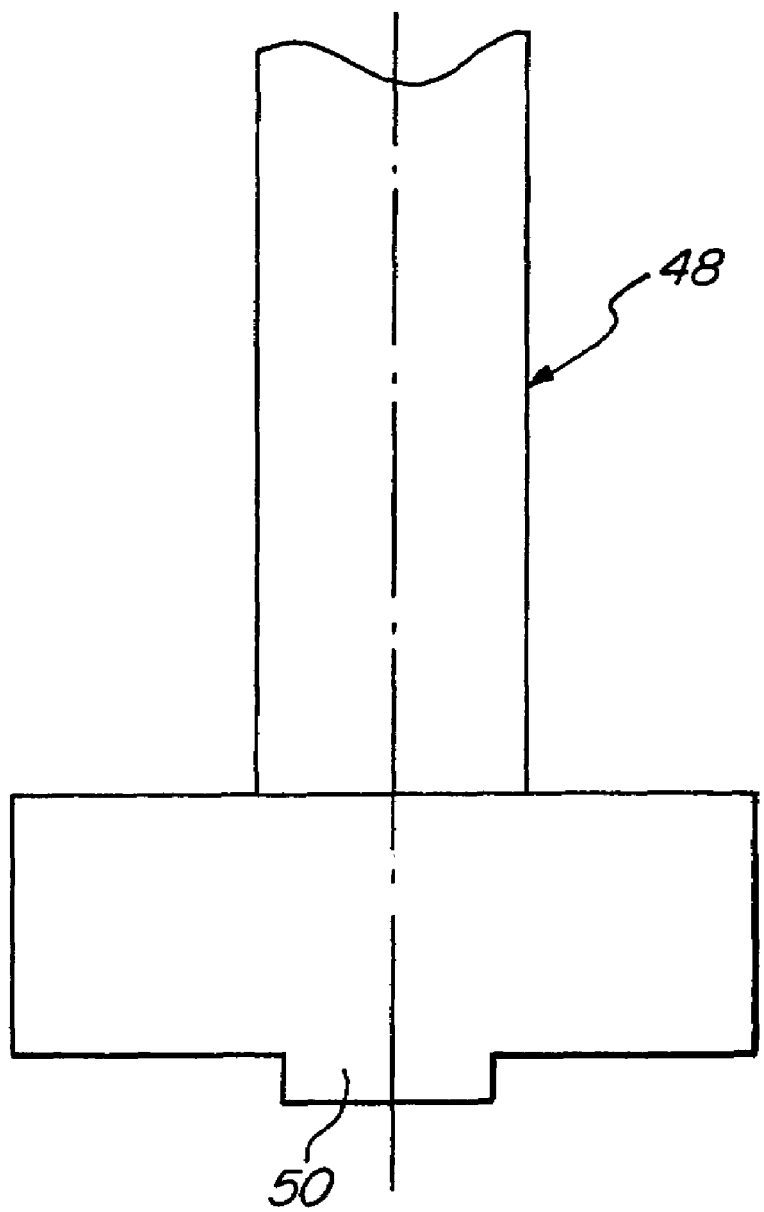
FIG. 9 is a fragmentary elevational view of the filler push rod of FIG. 8.

As seen in FIGS. 8 and 9, a push rod 48 has a projecting portion 50 dimensioned to bear upon the prongs 46 of the plug 28 to push the flange 44 off the front wall 36 to allow air to flow thereunder and thence about the body of the plug 28 through the piston 20.

Figure 10:
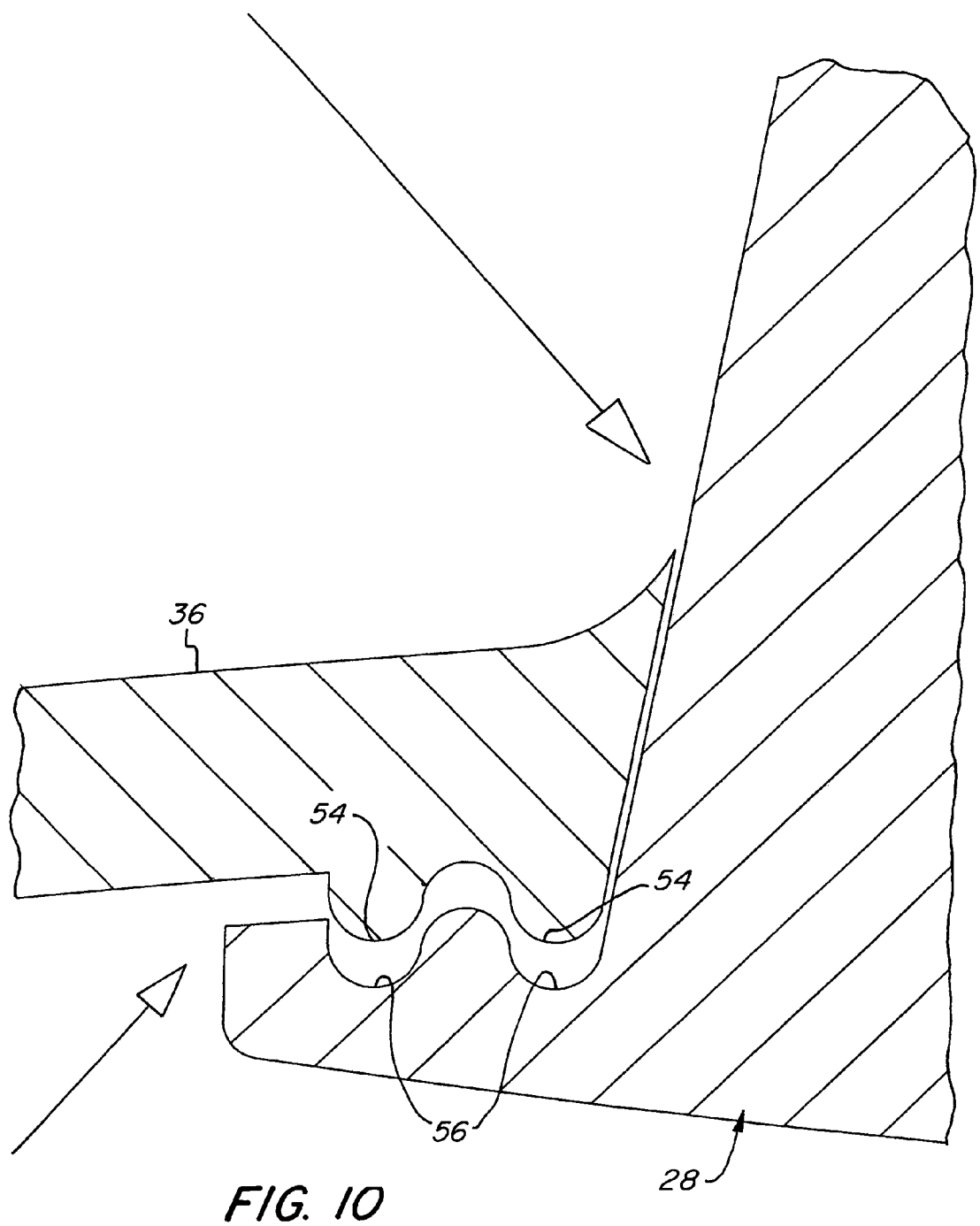
FIG. 10 is a fragmentary sectional view of the plug and piston body drawn to enlarged scale and showing the plug peripheral flange lifting from the front wall of the piston to allow air to pass thereabout.

Desirably, as seen in FIG. 10, the piston 20 is molded with a pair of circular ribs 54 in the front wall 36 and the flange 44 has circular grooves 56 which seat thereon to increase the sealing action.

As is well known, the resins selected for molding the piston and the plug as well as the container should be thermoplastic resins selected to provide resistance to degradation by the material to be placed therein. Generally, polyolefins and polyamides are suitable for most applications with polypropylene being preferred because of its strength and inertness.

The material used for the plunge and the peripheral seals must also be a thermoplastic resin and provide resilient deflectability and chemical resistance such as elastomers such as ethylene propylene terpolymers and other synthetic elastomers. The durometer of the elastomer should be in the range of 50–60 Shore A.

A resin which has been proven quite satisfactory are proprietary materials sold by Advanced Elastomer Systems, LP of Akron, Ohio, under the trade name SANTOPRENE which is described as thermoplastic elastomers.

The piston peripheral sears and the plug can be formed on the piston in an overmolding process after the resin of the piston has hardened.

In operation, the user places the material to be dispensed through the open end into the cavity of the syringe and then inserts the piston/plug assembly into the cavity over the material. Because the piston 20 seals against the peripheral wall 12 of the container 10, a volume of air is trapped therebelow and must be evacuated. A filler push rod such as that illustrated in FIG. 9 is then inserted and the piston is pushed towards the material in the cavity. Since the center projection on the push rod beard directly on the four prongs of the plug 28, this causes the peripheral flange to lift from the front wall 26 of the piston 20 to allow air to flow thereunder and thence about the body of the plug as shown in FIG. 10.

After all of the air has been evacuated, the filler push rod is removed and a conventional dispensing push rod (not shown) is inserted. This has a planar face that bears upon the rear face of the piston but not upon the plug 28 so that the contents may be displaced with leakage about the plug.

Thus, it can be seen from the foregoing detailed specification and the attached drawings that the dispenser of the present invention provides highly effective and trouble free evacuation of the air from the cavity after the product has been placed therein. Moreover, the piston for the dispenser may be fabricated readily and economically by an overmolding process.

Having thus described the invention, what is claimed is:

1. A dispenser comprising:
    (a) a container providing a cavity having an inner wall and a discharge opening at one end;
    (b) a piston in said cavity and having a peripheral wall portion sealing against the inner wall of the container defining said cavity, said piston having a front wall, a rear wall and a centrally disposed passage therethrough;
    (c) a sealing plug of resiliently deformable material seated in said passage with a front end and rear end and having a peripheral flange about said front end thereof adjacent the discharge opening, said flange bearing upon a surface of said front wall of said piston about said passage to effect a seal therebetween; and
    (d) a filler push rod extending into said container cavity and having one end bearing upon a surface of said sealing plug spaced from said discharge opening, said push rod being movable against said rear end of said plug to move said flange of said plug away from said surface of said piston to allow air to vent through said passage around the periphery of said plug.

2. The dispenser in accordance with claim 1 wherein said front wall of said piston is concave.

3. The dispenser in accordance with claim 1 wherein said piston has an annular body portion connected to said peripheral wall portion by said front wall, said front wall having a center portion radially inwardly of said annular body portion and in which said passage is provided.

4. The dispenser in accordance with claim 3 wherein said piston peripheral wall portion has at least one sealing ring extending thereabout adjacent said front wall thereof.

5. The dispenser in accordance with claim 4 wherein said piston peripheral wall portion has a second sealing ring extending thereabout adjacent said rear wall thereof.

6. The dispenser in accordance with claim 5 wherein said sealing rings are formed from a resiliently deflectable resin.

7. The dispenser in accordance with claim 1 wherein said front wall of said piston has a recess in the central portion thereof in which said plug is seated.

8. The dispenser in accordance with claim 1 wherein said plug has a convex face on its front end and a multiplicity of axial projections on the other end thereof against which said filler push rod may bear after filling of the cavity to cause the deflection of said flange and release any entrapped air in said cavity.

9. The dispenser in accordance with claim 8 wherein said filling push rod has a pusher body with a front end having a central projection thereon to bear upon only said plug.

10. The dispenser in accordance with claim 3 wherein a dispenser push rod used for the dispensing of the contents bears upon the body portion of said piston and does not effect deflection of said flange of said plug.

11. The dispenser in accordance with claim 7 wherein said plug has a peripheral surface tapering to a reduced diameter at its rear end.

\* \* \* \* \*